(12) United States Patent  
Tsao

(10) Patent No.: US 9,146,306 B2
(45) Date of Patent: Sep. 29, 2015

(54) ULTRASOUND DIAGNOSTIC APPARATUS

(75) Inventor: Jing-Wen Tsao, Mitaka (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 0 days.

(21) Appl. No.: 12/827,099

(22) Filed: Jun. 30, 2010

(65) Prior Publication Data

US 2011/0021921 A1 Jan. 27, 2011

(30) Foreign Application Priority Data

Jul. 21, 2009 (JP) .................. 2009-169817

(51) Int. Cl.
*G01S 7/52* (2006.01)
*G01S 15/89* (2006.01)
*G10K 11/34* (2006.01)
*A61B 8/00* (2006.01)

(52) U.S. Cl.
CPC ............ *G01S 7/5208* (2013.01); *G01S 15/8925* (2013.01); *G01S 15/8927* (2013.01); *G10K 11/346* (2013.01); *A61B 8/4494* (2013.01)

(58) Field of Classification Search
CPC ............ G01S 15/8925; G01S 15/8927; G01S 7/5208; G10K 11/346; A61B 8/4494
USPC ................................. 600/437, 459
See application file for complete search history.

(56) References Cited

U.S. PATENT DOCUMENTS

| 5,229,933 A | 7/1993 | Larson, III |
| 5,563,346 A | 10/1996 | Bartelt et al. |
| 5,784,336 A | 7/1998 | Gopinathan et al. |
| 5,997,479 A | 12/1999 | Savord et al. |
| 6,126,602 A | 10/2000 | Savord et al. |
| 6,868,729 B2 | 3/2005 | Amemiya |
| 7,090,642 B2 | 8/2006 | Satoh |
| 7,217,243 B2 | 5/2007 | Takeuchi |

(Continued)

FOREIGN PATENT DOCUMENTS

| CN | 1575772 A | 2/2005 |
| EP | 0 430 450 A2 | 6/1991 |

(Continued)

OTHER PUBLICATIONS

Japanese Office Action dated Jul. 26, 2011, issued in corresponding Japanese Patent Application No. 2009-169817.

(Continued)

*Primary Examiner* — Katherine Fernandez
(74) *Attorney, Agent, or Firm* — Westerman, Hattori, Daniels & Adrian, LLP

(57) ABSTRACT

A 2D array transducer 10 is separated into a plurality of sub-arrays. Four representative sub-arrays from SA1 to SA4 are shown in an enlarged manner. In addition, the 2D array transducer (10) is segmented into a plurality of transducer regions. Four regions of (I)-(IV) segmented by dot-and-chain lines represent four transducer regions. For each sub-array, a delay process corresponding to the sub-array is executed based on a delay pattern defining an amount of delay for each of the plurality of transducer elements belonging to the sub-array. In this process, for each transducer region, a common delay pattern is set for the plurality of sub-arrays belonging to the transducer region. For example, because sub-arrays SA1 and SA2 belong to the same transducer region (IV), a common delay pattern is set for the sub-arrays SA1 and SA2.

12 Claims, 5 Drawing Sheets

(56) References Cited

U.S. PATENT DOCUMENTS

| | | |
|---|---|---|
| 2004/0066708 A1 | 4/2004 | Ogawa |
| 2004/0267126 A1 | 12/2004 | Takeuchi |
| 2005/0243812 A1* | 11/2005 | Phelps .......................... 370/360 |
| 2006/0253034 A1 | 11/2006 | Fukukita |
| 2008/0146930 A1 | 6/2008 | Takeuchi |
| 2008/0146938 A1 | 6/2008 | Hazard et al. |
| 2008/0234585 A1 | 9/2008 | Iwama |
| 2008/0262351 A1 | 10/2008 | Scampini |
| 2009/0306510 A1 | 12/2009 | Hashiba et al. |

FOREIGN PATENT DOCUMENTS

| | | |
|---|---|---|
| EP | 1 936 404 A1 | 6/2008 |
| JP | 61-52864 A | 3/1986 |
| JP | 2-182245 A | 7/1990 |
| JP | 4-254754 A | 9/1992 |
| JP | 10-179585 A | 7/1998 |
| JP | 2000-033087 A | 2/2000 |
| JP | 2001-286467 A | 10/2001 |
| JP | 2004-105257 A | 4/2004 |
| JP | 2005-034633 A | 2/2005 |
| JP | 2005-102717 A | 4/2005 |
| JP | 2005-270423 A | 10/2005 |
| JP | 2005-342194 A | 12/2005 |
| JP | 3977827 B2 | 9/2007 |
| JP | 2008-514335 A | 5/2008 |
| JP | 2008-229096 A | 10/2008 |
| WO | 2005/019856 A1 | 3/2005 |
| WO | 2006-134686 A1 | 12/2006 |

OTHER PUBLICATIONS

European Search Report dated Nov. 29, 2010, issued in corresponding European Patent Application No. 10006737.0.
Office Action issued in European Patent Office on Nov. 22, 2011 in corresponding European Patent Application No. 10006737.0.
Chinese Office Action dated Mar. 29, 2013, issued in corresponding Chinese Patent Application No. 201010234562; with English Translation (11 pages).
Office Action issued May 20, 2013 in related Chinese Patent Application 201010238951.4 (11pages). English translation.
Final Office Action dated Jan. 10, 2013 issued in U.S. Appl. No. 12/833,472 (17 pages).
Non-Final Office Action dated Jul. 18, 2013, issued in U.S. Appl. No. 12/833,472 (17 pages).
Summons to attend oral pursuant to Rule 115(1) EPC dated Nov. 4, 2013, issued in corresponding European Patent Application No. 10006737.0 (5 pages).
Office Action issued on Jul. 4, 2012 in corresponding Chinese Patent Application No. 201010234562.4. English Translation.
European Search Report dated Nov. 30, 2010, issued in corresponding European Patent Application No. 10007109.1 (8 pages).
European Office Action dated Feb. 8, 2012, issued in corresponding European Patent Application No. 10007109.1 (6 pages).
Office Action issued in European Patent Office on Nov. 22, 2011, in corresponding European Patent Application No. 10 006 737.0 (6 pages).
Chinese Office Action dated Aug. 30, 2012, issued in corresponding Chinese Patent Application No. 201010238951.4 with English translation (11 pages).
Non-Final Office Action dated Aug. 17, 2012, issued in U.S. Appl. No. 12/833,472 (26 pages).
European Decision to refuse a European Patent Application dated Feb. 21, 2014, issued in corresponding European Patent Application No. 10006737.0 (30 page).
European Provision of the minutes in accordance with Rule 124(4)EPC dated Feb. 21, 2014, issued in corresponding European Patent Application No. 10006737.0, (11 pages).
Japanese Office Action dated Feb. 19, 2013, issued in corresponding Japanese Patent Application No. 2009-169817, with English translation (9 pages).
Chinese Office Action dated Dec. 12, 2013, issued in corresponding Chinese Patent Application No. 201010238951.4 with English translation(13 pages).
European Summons to attend oral proceedings pursuant to Rule 115(1) EPC dated Nov. 27, 2013, issued in corresponding European Patent Application No. 10007109.1(5 pages).
Office Action dated Jul. 30, 2013, issued in corresponding Japanese application No. 2009-175440, with English Translation.
Provision of the minutes in accordance with Rule 124(4)EPC dated May 23, 2014, issued in corresponding European Patent Application No. 10007109.1 (12 pages).
Decision to Refuse a European Patent Application dated May 23, 2014, issued in corresponding European Patent Application No. 10007109.1 (26 pages).

* cited by examiner

ULTRASOUND DIAGNOSTIC APPARATUS

BACKGROUND

1. Technical Field

The present invention relates to an ultrasound diagnostic apparatus, and, in particular, to a technique for forming an ultrasound beam using an array transducer.

2. Background Art

Two-dimensional array transducers constructed by two-dimensionally arranging a plurality of transducer elements are known. The two-dimensional array transducer is formed, for example, with a few thousand transducer elements which are electrically controlled. With the two-dimensional array transducer, ultrasound beams are two-dimensionally scanned, and echo data are three-dimensionally collected.

When a plurality of transducer elements which are a part of the two-dimensional array transducer are controlled, if a signal line is provided independently for each transducer element, a number of signal lines equaling the total number of transducer elements; for example, a few thousand signal lines, would be required for the overall two-dimensional array transducer. When a few thousand signal lines are employed, a probe cable connecting a probe in which the transducer elements are stored and a device body would become thick, and the number of pins of the connector in a connection portion between the probe cable and the device body also becomes large. The increase in circuit size for transmission/reception systems cannot be ignored. In consideration of these circumstances, techniques have been proposed for reducing the number of signal lines (number of channels) connecting the plurality of transducer elements and the device body.

For example, Patent Literature 1 (JP 2008-514335A) discloses a technique in which the two-dimensional array transducer is separated into a plurality of sub-arrays, reception signals of, for example, nine (three in vertical×three in lateral) transducer elements in each sub-array are delay-added, to sum signal of each sub-array into one signal at the side of the probe, and, then, the one signal line is connected to the device body. With such a structure, the number of channels can be significantly reduced to, for example, 1/9.

In order to sum the sub-array signals into one signal, information of amount of delay for each of, for example, nine transducer elements belonging to the sub-array is required, and the information is supplied from the device body to the probe. When the amount of delay is adjusted according to a steering angle of the beam and a depth of focus, the amount of the information to be supplied from the device body to the probe becomes very high. For example, when the amounts of delay for a few thousand transducer elements are transferred, a transfer time of a few tens of microseconds would be required, which may result in other problems, such as reduction in the frame rate.

Patent Literature 2 (JP 2000-33087 A) discloses a technique to apply a control such that the depth of focus is fixed at infinity and only the beam steering is considered, to simplify the control of delay and reduce the amount of information. However, when the depth of the focus is simply set to infinity, converging of the beam etc. may be degraded and the precision of the beamforming is reduced, resulting in reduction in the resolution or the like of the image.

Under such circumstances, the present inventor have researched and developed a technique which maintains the precision of the beamforming while inhibiting increase in the amount of information of the delay process.

SUMMARY

The present invention was conceived in the above-described research and development process, and an advantage of the present invention is that an improved technique is provided for forming an ultrasound beam using an array transducer.

According to one aspect of the present invention, there is provided an ultrasound diagnostic apparatus comprising an array transducer comprising a plurality of transducer elements and divided into a plurality of sub-arrays, and a sub-array processor which executes, for each sub-array, a delay process corresponding to each sub-array based on a delay pattern defining an amount of delay for each of a plurality of the transducer elements belonging to the sub-array, wherein the array transducer is segmented into a plurality of transducer regions, and, for each transducer region, a common delay pattern is set for the plurality of sub-arrays belonging to the transducer region.

With the ultrasound diagnostic apparatus of the above-described configuration, because, for each transducer region, a common delay pattern is set for a plurality of sub-arrays belonging to the transducer region, the amount of information related to the delay pattern can be reduced as compared with a case where an individual delay pattern is set for each of the plurality of sub-arrays. In addition, because the delay pattern is set corresponding to each of the plurality of transducer regions, the precision of the beamforming such as the converging of the beam can be improved as compared with a case where a common delay pattern is set for the entire array transducer.

With the present invention, an improved technique for forming the ultrasound beam using the array transducer is provided. For example, because, for each transducer region, a common delay pattern is set for the plurality of sub-arrays belonging to the transducer region, the amount of information related to the delay pattern can be reduced as compared with a case where an individual delay pattern is set for each of the plurality of sub-arrays. In addition, because a delay pattern corresponding to each of the plurality of transducer regions is set, the precision of the beamforming such as the converging of the beam can be improved as compared with a case where a common delay pattern is set for the entire array transducer.

DESCRIPTION OF EMBODIMENT

A preferred embodiment of the present invention will now be described.

Figure 1:
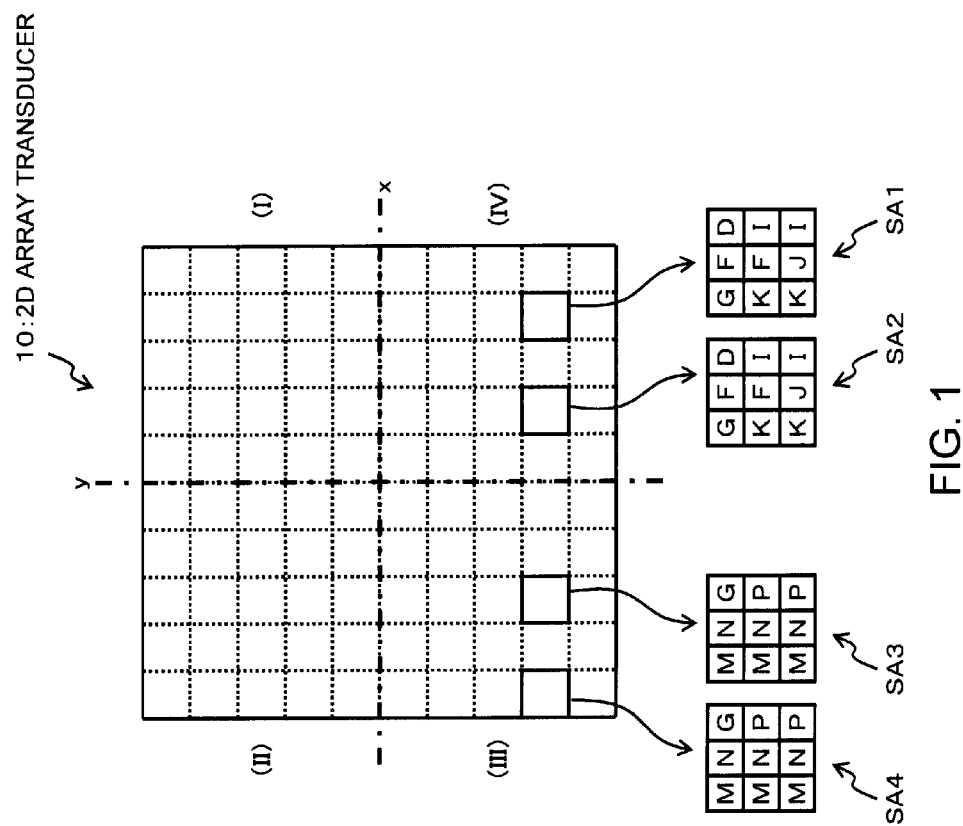
FIG. 1 is a diagram showing a 2D array transducer of an ultrasound diagnostic apparatus of a preferred embodiment of the present invention.

FIG. 1 is a diagram showing a two-dimensional (2D) array transducer 10 of an ultrasound diagnostic apparatus of a preferred embodiment of the present invention. The 2D array transducer 10 is formed by two-dimensionally arranging a plurality of transducer elements. For example, a plurality of transducer elements are two-dimensionally arranged in a vertical direction and a lateral direction, and a transducer surface of the 2D array transducer 10 is formed in a square shape as shown in FIG. 1. Alternatively, the plurality of transducer elements may be two-dimensionally arranged in a circular shape so that the transducer surface of the 2D array transducer 10 is formed in a circular shape.

The 2D array transducer 10 is divided into a plurality of sub-arrays. In FIG. 1, each of a plurality of squares separated in a lattice shape by a dotted line represents a sub-array. FIG. 1 shows in an enlarged manner four sub-arrays SA1-SA4 as representative sub-arrays. Each sub-array comprises a plurality of transducer elements. For example, each sub-array comprises nine transducer elements. In FIG. 1, nine squares arranged in a lattice shape in each sub-array of SA1-SA4 represent nine transducer elements.

In addition, the 2D array transducer 10 is segmented into a plurality of transducer regions. In FIG. 1, four regions (quadrants) of (I)-(IV) segmented by x-axis and y-axis of a dot-and-chain line represent four transducer regions. In FIG. 1, each of the transducer regions (I)-(IV) comprises 25 sub-arrays. It should be noted that FIG. 1 merely exemplifies one configuration for the preferred embodiment of the present invention, and the number of transducer elements in each sub-array and the number of sub-arrays in each transducer region are not limited to those in the example configuration of FIG. 1.

A plurality of transducer elements of the 2D array transducer 10 are electronically controlled, and, with this configuration, the ultrasound beam is two-dimensionally scanned and three-dimensional echo data are collected. In the electronic control, an amount of delay (delay time) corresponding to each transducer element is set. For example, a transmitted signal which is delayed by the amount of delay corresponding to each transducer element is supplied to the transducer element, and a transmission beam is formed by a plurality of transducer elements of the 2D array transducer 10. In addition, for example, after the delay process by the amount of delay corresponding to each transducer element is applied to a reception signal obtained from the transducer element, the reception signals of a plurality of transducer elements of the 2D array transducer 10 are added, to form a reception signal along the reception beam.

In the present embodiment, the delay process corresponding to each sub-array is executed based on a delay pattern defining, for each sub-array, an amount of delay for each of the plurality of transducer elements belonging to the sub-array. In addition, for each transducer region, a common delay pattern is set for a plurality of sub-arrays belonging to the transducer region.

For example, because the sub-arrays SA1 and SA2 shown in FIG. 1 belong to the same transducer region (transducer region (IV)), a common delay pattern is set for the sub-array SA1 and the sub-array SA2. In FIG. 1, the letters assigned to the transducer elements in the sub-arrays SA1 and SA2 indicate the amounts of delay for the transducer elements, and the same letter represents the same amount of delay. The arrangement pattern of the letters in the sub-array SA1 and the arrangement pattern of the letters in the sub-array SA2 match each other. In other words, the arrangement pattern of the amounts of delay for the plurality of transducer elements in the sub-array SA1 and the arrangement pattern of the amounts of delay for the plurality of transducer elements in the sub-array SA2 match each other.

Similarly, because the sub-arrays SA3 and SA4 shown in FIG. 1 belong to the same transducer region (transducer region (III)), a common delay pattern is set for the sub-arrays SA3 and SA4.

In setting the common delay pattern in each transducer region, a virtual plane is correlated to each of the plurality of transducer regions, and, for each transducer region, a common delay pattern is set based on the correlated virtual plane.

A second order approximation equation of a delay time $\tau$ for the plurality of transducer elements of the 2D array transducer 10 can be split into a term S which depends on steering and a term F which depends on focus. The delay time $\tau$ can be represented as follows as a quadratic function of coordinates x and y.

[Equation 1]

$$\tau c = S - F \quad (1)$$

$$S = x \sin\theta_x + y \cos\theta_x \sin\theta_y \quad (2)$$

$$F = (x^2 + y^2 - S^2)/2f \quad (3)$$

Here, c represents the velocity of sound, $\theta_x$ represents a steering angle in the x direction, $\theta_y$ represents a steering angle in the y direction, and f represents a focus distance (depth). When the focus distance f is infinity, the focus-dependent term F becomes 0 (F=0), and $\tau c$ is represented as follows with only the steering-dependent term S.

[Equation 2]

$$\tau c = \alpha x + \beta y \quad (4)$$

$\alpha = \sin\theta_x$, $\beta = \cos\theta_x \sin\theta_y$

In other words, $\tau c$ becomes a linear equation of a plane. The slopes of the plane in the x direction and the y direction are $\alpha$ and $\beta$, which are known and related to steering. Because the function is a linear function, a difference in delay time between transducer elements is a constant proportional to the slopes $\alpha$ and $\beta$, and the delay patterns of all sub-arrays in the 2D array transducer 10 are set identical to each other. However, in this case, the focus distance f is infinity.

Next, with the focus distance f being finite, the focus-dependent term F which is approximated in quadratic form is also approximated with an equation of a plane as follows.

[Equation 3]

$$F = a_i x + b_i y \quad [i = 1 \sim 4] \quad (5)$$

Here, for the focus-dependent term F, slopes $a_i$ and $b_i$ are determined for each transducer region. The index i represents the numbers 1-4 of transducer regions (for example, I-IV in FIG. 1).

When the equation of plane of Equation (5) is used for the focus-dependent term F, $\tau c$ which is represented with Equation (4) only by the steering-dependent term S can be expanded as follows.

[Equation 4]

$$\tau c = \alpha x + \beta y - (a_i x + b_i y) = (\alpha - a_i)x + (\beta - b_i)y \quad [i = 1 \sim 4] \quad (6)$$

In Equation (6), for each of i=1~4; that is, for each transducer region, a linear equation of a plane is determined. Because of this, the delay patterns for a plurality of sub-arrays become identical in each transducer region.

In Equation (5), the slopes of a plane $a_i$ and $b_i$ must be determined for each transducer region. For example, the slopes $a_i$ and $b_i$ can be determined by setting a regression plane by the least squares method using Equations (3) and (5). In this case, when the number of transducer elements in each transducer element region is N, the slopes $a_i$ and $b_i$ can be calculated by the following equations.

[Equation 5]

$$a_i = \frac{\sum_{n=1}^{N} y_n^2 \cdot \sum_{n=1}^{N} x_n F_n - \sum_{n=1}^{N} x_n y_n \cdot \sum_{n=1}^{N} y_n F_n}{d} \quad (7)$$

$$b_i = \frac{\sum_{n=1}^{N} x_n^2 \cdot \sum_{n=1}^{N} y_n F_n - \sum_{n=1}^{N} x_n y_n \cdot \sum_{n=1}^{N} x_n F_n}{d}$$

$$d = \sum_{n=1}^{N} x_n^2 \cdot \sum_{n=1}^{N} y_n^2 - \left(\sum_{n=1}^{N} x_n y_n\right)^2 \quad (8)$$

Alternatively, the slops $a_i$ and $b_i$ may be determined by iterative numerical calculations, without the use of Equations (7) and (8). When, for example, a distribution of the plurality of transducer elements of the 2D array transducer 10 is circular and symmetric about the center of the circle, $a_1=-a_3$, $b_1=-b_3$, $a_2=-a_4$, and $b_2=-b_4$.

A common delay pattern is set for a plurality of sub-arrays in each transducer region as described above, and an amount of sub-delay is set for each transducer element according to the delay pattern. In addition, in the present embodiment, an individual amount of main delay is set for each of the plurality of sub-arrays.

Figure 2:
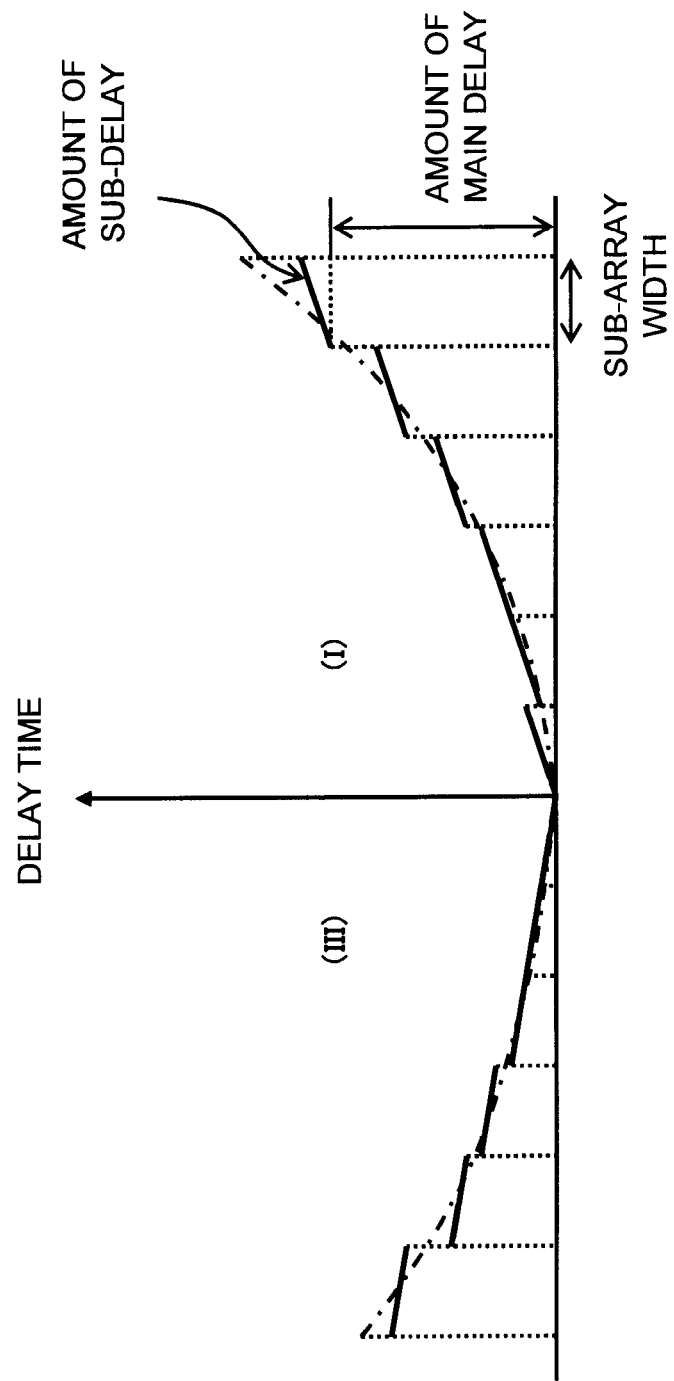
FIG. 2 is a diagram for explaining an amount of sub-delay and an amount of main delay.

FIG. 2 is a diagram for explaining the amount of sub-delay and the amount of main delay, and is a conceptual diagram showing setting of the amount of delay for the transducer region (I) and the transducer region (III) of FIG. 1. In FIG. 2, the horizontal axis represents a position of the transducer element, and a plurality of sub-arrays are arranged along the horizontal axis direction, with a width of the sub-array being a constant sub-array width. The vertical axis of FIG. 2 represents a magnitude of the amount of delay (delay time).

In the present embodiment, a common delay pattern is set for the plurality of sub-arrays in each transducer region. Because of this, in FIG. 2, an amount of sub-delay having a common slope (inclination) is set for the plurality of sub-arrays belonging to, for example, the transducer region (I).

In addition, in the present embodiment, an individual amount of main delay is set for each of the plurality of sub-arrays. A sum of the amount of main delay and the amount of sub-delay is set as the amount of delay for each transducer element.

The amount of delay obtained as a sum of the amount of main delay and the amount of sub-delay is set to approach an ideal delay curve. In FIG. 2, a curve shown with a dot-and-chain line represents the ideal delay line. The amount of main delay and the amount of sub-delay are suitably adjusted such that the delay pattern of the stairs-shape obtained as a sum of the amounts of delay is along the ideal delay curve. With this configuration, degradation of the beam characteristic can be inhibited.

Figure 3:
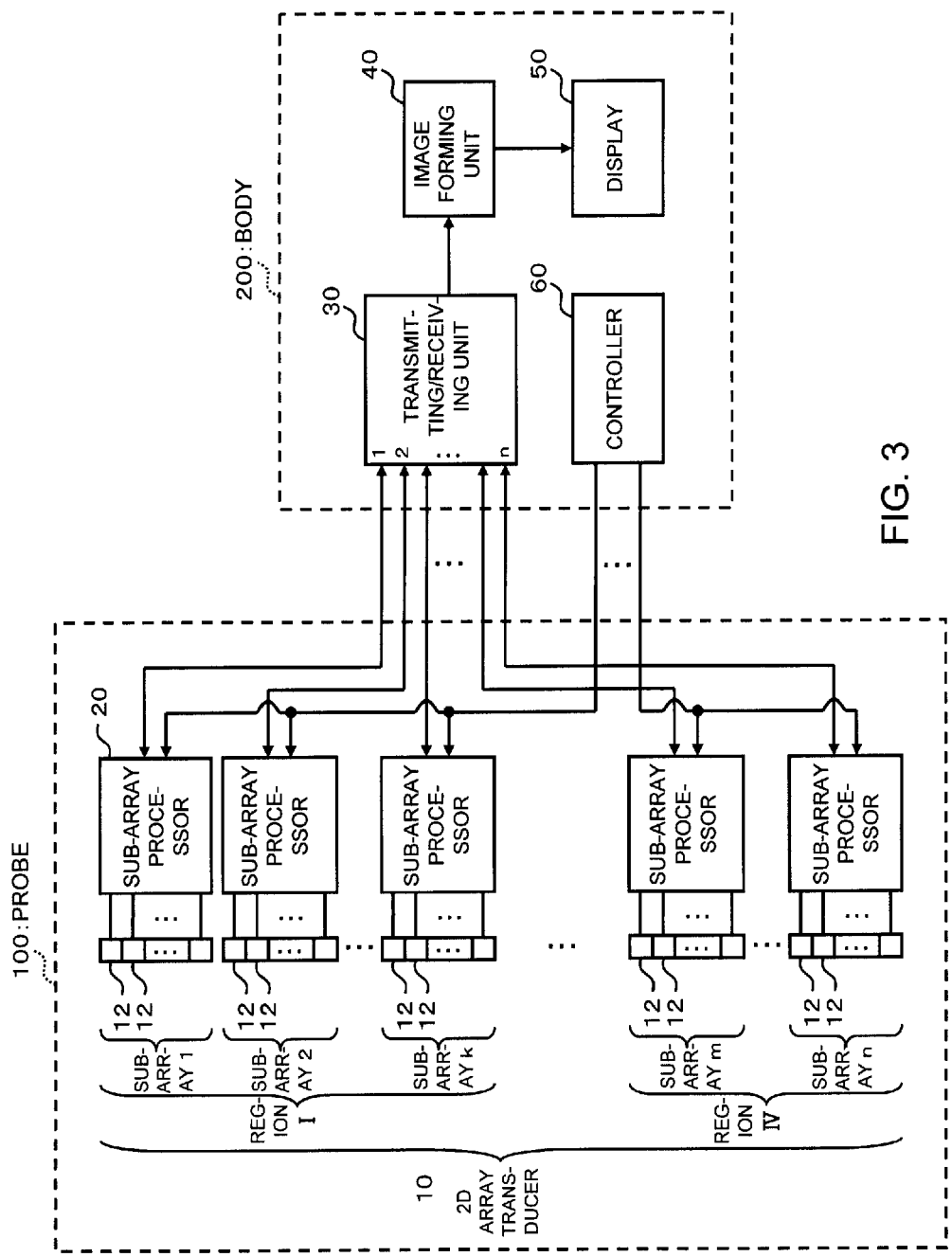
FIG. 3 is a diagram showing the overall structure of an ultrasound diagnostic apparatus of the preferred embodiment of the present invention.

FIG. 3 is a diagram showing the overall structure of an ultrasound diagnostic apparatus of the present embodiment. The ultrasound diagnostic apparatus of FIG. 3 comprises a probe 100 and a body 200, and the probe 100 and the body 200 are connected to each other via a cable.

The probe 100 comprises the 2D array transducer 10 (refer to FIG. 1). The 2D array transducer 10 is constructed by two-dimensionally arranging the plurality of transducer elements 12. In addition, the 2D array transducer 10 is divided into a plurality of sub-arrays 1~n and segmented into a plurality of transducer regions I~IV.

A sub-array processor 20 is provided for each of the plurality of sub-arrays 1~n. The sub-array processor 20 executes a delay process corresponding to the sub-array. In the delay process, the delay pattern which is set for each sub-array is used.

The device body 200 comprises a transmitting/receiving unit 30. During transmission, the transmitting/receiving unit 30 outputs a transmitted signal to which a delay process for individual amount of main delay for each sub-array is applied to each of the plurality of sub-array processors 20. The sub-array processor 20 applies a delay process to the transmitted signal by the amount of sub-delay corresponding to each transducer element 12 based on the delay pattern, and outputs the transmitted signal to each transducer element 12. In this manner, the transmitted signal to which the delay process is applied is supplied to the plurality of transducer elements 12 of the 2D array transducer 10, and the transmission beam is formed.

Meanwhile, at the reception, each sub-array processor 20 applies a delay process on the reception signal obtained from each transducer element 12 based on the delay pattern, and adds the reception signals after the delay process, obtained from the plurality of transducer elements 12 belonging to the sub-array. The reception signal to which the addition process is applied for each sub-array processor 20 is sent to the transmitting/receiving unit 30. The transmitting/receiving unit 30 applies a delay process by an individual amount of main delay for each sub-array processor 20 to the reception signal obtained from each sub-array processor 20, and adds the reception signals after the delay process, obtained from the plurality of sub-array processors 20. In this manner, the reception signals obtained from the plurality of transducer elements 12 of the 2D array transducer 10 are collected, and echo data along the reception beam are obtained.

In each sub-array processor 20, the delay pattern used in transmission and the delay pattern used in reception may be a common pattern or may be different delay patterns between transmission and reception. Alternatively, at the reception, the amount of main delay related to each of the plurality of sub-array processors 20 may be suitably controlled, to obtain echo data while changing the focus depth of the reception beam. In other words, the amount of main delay may be controlled to achieve a reception dynamic focus.

An image-forming unit 40 forms image data based on echo data obtained along a plurality of reception beams. An ultrasound image corresponding to the image data is displayed on a display 50. For example, the ultrasound beam is two-dimensionally scanned and echo data are three-dimensionally collected, and a three-dimensional ultrasound image is formed. Alternatively, a two-dimensional ultrasound image may be formed.

A controller 60 integrally controls each unit of the ultrasound diagnostic apparatus of FIG. 3. In particular, the controller 60 outputs control data for setting the delay pattern to the plurality of sub-array processors 20.

In the present embodiment, a common delay pattern is set for a plurality of sub-arrays in each transducer region. Because of this, the controller 60 may output the same control data to the plurality of sub-arrays processors 20 belonging to the same transducer region. For example, common control data are output to a plurality of sub-array processors 20 belonging to the region I. Therefore, the controller 60 may output control data of a number corresponding to the number of transducer regions (for example, four).

Figure 4:
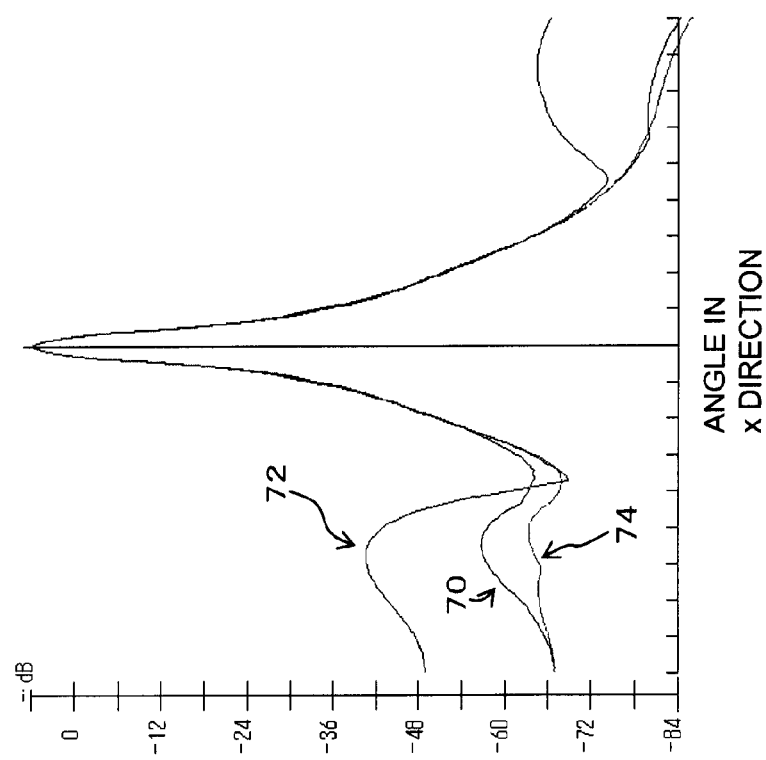
FIG. 4 is a diagram showing a comparison result related to precision of a beamforming.

FIG. 4 is a diagram showing a comparison result related to precision of the beamforming. FIG. 4 shows a beam characteristic in the x direction by a sound field simulation. The horizontal axis of FIG. 4 shows an angle in the x direction and the vertical axis represents an intensity of the sound field.

FIG. 4 shows comparison results of three patterns related to the delay control. A waveform 72 represents a sound field characteristic in a case where the amount of delay is set for each transducer element while the focus distance is set to infinity and only the steering is considered (refer to Equation (4)). A waveform 74 represents a sound field characteristic when the amount of delay is set for each transducer element according to an ideal curve.

A waveform 70, meanwhile, represents a sound field characteristic resulting from the configuration of the present embodiment. In other words, the waveform 70 represents a sound field characteristic when a common delay pattern is set for a plurality of sub-arrays in each transducer region, and an individual amount of main delay is set for each of the plurality of sub-arrays.

Upon comparison of the three patterns, it can be seen that there is no significant difference in the main lobe where the intensity of the sound field becomes the maximum. However, in the grating lobe in which the sound field shows a tendency of maximum at a position deviated from the main lobe, a notable difference occurs among the three patterns.

In the beam characteristic, the grating lobe is desirably small. Of the three patterns, in the waveform 74, because the amount of delay is set for each transducer element according to the ideal curve, the grating lobe is the smallest, and superior beamforming precision is achieved. In the waveform 72, because the beam control is a simplified control which sets the focus distance to infinity and considers only the steering, the grating lobe is the largest and the beamforming precision is inferior.

The waveform 70, which is the sound field resulting from the configuration of the present embodiment, in contrast, has a smaller grating lobe compared to the waveform 72, and the grating lobe is inhibited to a level very close to that of the waveform 74.

The waveform 74 is the sound field characteristic when the amount of delay is set for each transducer element according to the ideal curve. However, in order to set the amount of delay for each transducer element, a huge amount of information for the amount of delay is required. On the other hand, in the waveform 70, which is the sound field characteristic resulting from the configuration of the present embodiment, because the only requirement is to set a common delay pattern to the plurality of sub-arrays in each transducer region, the amount of information for the amount of delay can be maintained at a low level. For example, if the individual delay pattern is to be set for each of 164 sub-arrays, 164 delay patterns would be required, but in the present embodiment, 4 delay patterns corresponding to the 4 transducer regions may be set. In other words, the number of delay patterns can be dramatically reduced from 164 to 4.

As described, according to the present embodiment, the precision of the beamforming can be maintained while reducing the number of delay patterns.

Figure 5:
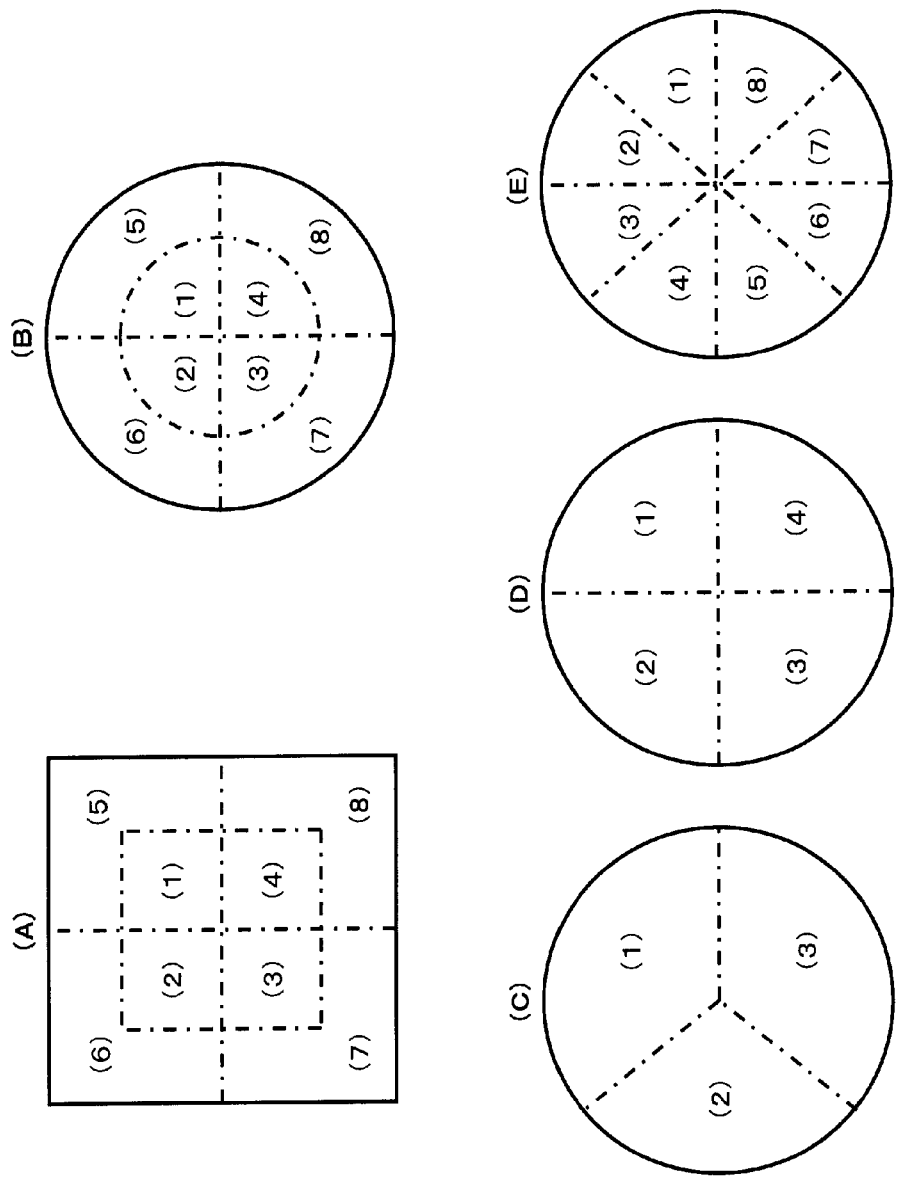
FIG. 5 is a diagram showing various segmenting patterns of the transducer region.

FIG. 5 is a diagram showing various segmenting patterns of the transducer regions. In each of patterns (A)-(E), squares and circles surrounded by solid lines represent a transducer surface of the 2D array transducer, and a dot-and-chain line drawn within the transducer surface represents a boundary of the transducer region.

The 2D array transducer is segmented into a plurality of transducer regions by a virtual boundary radially extending from the center of the transducer surface, and is further segmented, as necessary, into a plurality of transducer regions by a virtual boundary which is set to surround the center of the transducer surface.

In pattern (A), a square transducer surface is segmented into 8 transducer regions (1)-(8). In pattern (B), a circular transducer surface is segmented into 8 transducer regions (1)-(8). In addition, patterns (C)-(E) show example segmenting patterns for a circular transducer surface.

As described, various segmenting patterns can be employed for the transducer regions, and segmenting patterns other than the segmenting patterns shown in FIGS. 1 and 5 may be used.

A preferred embodiment of the present invention has been described. However, it should be noted that the above-described preferred embodiment is merely exemplary and does not limit the scope of the present invention.

What is claimed is:

1. An ultrasound diagnostic apparatus comprising:
an array transducer divided into a plurality of sub-arrays each containing a plurality of transducer elements; and
a sub-array processor connected to each of the plurality of sub-arrays, the sub-array processor configured to execute, for each sub-array, a delay process corresponding to the sub-array based on a delay pattern defining an amount of delay for each of the plurality of the transducer elements belonging to the sub-array, wherein
the array transducer is segmented into a plurality of transducer regions each containing a plurality of sub-arrays, and, for each transducer region, said sub-array processor configured to set a common delay pattern for the plurality of sub-arrays belonging to the transducer region,
wherein the delay process includes setting an amount of sub-delay having a common slope and an individual amount of main delay for each of the plurality of sub-arrays belonging to a respective transducer region, and
summing the amount of the sub-delay and the individual amount of the main delay to obtain the delay pattern that defines the amount of delay as the sum of the amount of the sub-delay and the individual amount of the main delay for each of the plurality of the transducer elements,
wherein the common slope is based on a difference in a delay time between the transducer elements contained within each of the sub-arrays over a difference in a sub-array width between the transducer elements contained within each of the sub-arrays.

2. The ultrasound diagnostic apparatus according to claim 1, wherein
the sub-array processor is further configured to determine a virtual plane and correlate the virtual plane to each of the plurality of transducer regions, and, for each transducer region, the common delay pattern is set based on the virtual plane correlated to the transducer region.

3. The ultrasound diagnostic apparatus according to claim 2, wherein
the sub-array processor is further configured to assign a beam steering angle to each of the plurality of transducer regions, and, for each transducer region, the virtual plane is correlated according to the assigned beam steering angle.

4. The ultrasound diagnostic apparatus according to claim 1, wherein
the sub-array processor is further configured to control a beam depth based on the individual amount of main delay which is set for each of the plurality of sub-arrays.

5. The ultrasound diagnostic apparatus according to claim 4, wherein the array transducer is a two-dimensional array transducer comprising a plurality of transducer elements which are two-dimensionally arranged.

6. The ultrasound diagnostic apparatus according to claim 1, wherein
the array transducer is a two-dimensional array transducer comprising a plurality of transducer elements which are two-dimensionally arranged.

7. The ultrasound diagnostic apparatus according to claim 6, wherein
the two-dimensional array transducer is segmented into the plurality of transducer regions by a virtual boundary radially extending from a center of a transducer surface.

8. The ultrasound diagnostic apparatus according to claim 7, wherein
the two-dimensional array transducer is segmented into the plurality of transducer regions by a virtual boundary which is set to surround the center of the transducer surface.

9. The ultrasound diagnostic apparatus according to claim 8, wherein
the two-dimensional array transducer is segmented into three or more transducer regions.

10. The ultrasound diagnostic apparatus according to claim 7, wherein
the two-dimensional array transducer is segmented into three or more transducer regions.

11. The ultrasound diagnostic apparatus according to claim 6, wherein
the two-dimensional array transducer is segmented into three or more transducer regions.

12. The ultrasound diagnostic apparatus according to claim 1, wherein
the array transducer is a two-dimensional array transducer comprising a plurality of transducer elements which are two-dimensionally arranged.

* * * * *